United States Patent [19]
Prahl

[11] 3,991,424
[45] Nov. 16, 1976

[54] COMPRESSION SHEATH FOR BELOW KNEE AMPUTATED LIMBS

[75] Inventor: Jan Prahl, Luneburg, Germany

[73] Assignee: IPOS Gesellschaft Fur integrierte Prothesen-Entwicklung und orthopadietechnischen Service mbH & Co., KG, Luneburg, Germany

[22] Filed: June 9, 1975

[21] Appl. No.: 584,915

Related U.S. Application Data

[63] Continuation-in-part of Ser. No. 501,816, Aug. 29, 1974, abandoned, which is a continuation of Ser. No. 342,934, March 2, 1973, abandoned.

[30] Foreign Application Priority Data

Mar. 20, 1972 Germany............................ 2213336

[52] U.S. Cl............................................. 3/1; 3/19; 128/157; 128/165
[51] Int. Cl.² ...................... A61F 1/00; A61F 13/06
[58] Field of Search ...................... 3/17–19, 3/1; 128/165, 157

[56] References Cited
UNITED STATES PATENTS 2,574,873  11/1951  Jobst................................ 128/165
2,807,946  10/1957  Virchaux ........................ 128/165 X

FOREIGN PATENTS OR APPLICATIONS 1,445,063  5/1966  France........................................ 3/19

Primary Examiner—Ronald L. Frinks
Attorney, Agent, or Firm—Toren, McGeady and Stanger

[57] ABSTRACT

A tubular compression sheath formed of a resilient yarn or fabric is structured to comprise a band defining an upper open end and an oppositely disposed enclosed end with an intermediate portion extending therebetween. The intermediate portion is formed in two sections, with the lower of said two intermediate sections having a knitted pattern with a higher yarn density than the upper intermediate section. The diameter of the sheath progressively decreases from the upper open end toward the lower enclosed end and the intermediate section is preferably formed from yarn having a thickness within a range between about 30 to 44 dtex. The preferred material from which the intermediate section is formed is Nylon 66 HE crimped. The sheath provides a desired radial compression about the limb upon which it is worn without producing undesired axial frictional forces across the area of the intermediate section.

7 Claims, 1 Drawing Figure

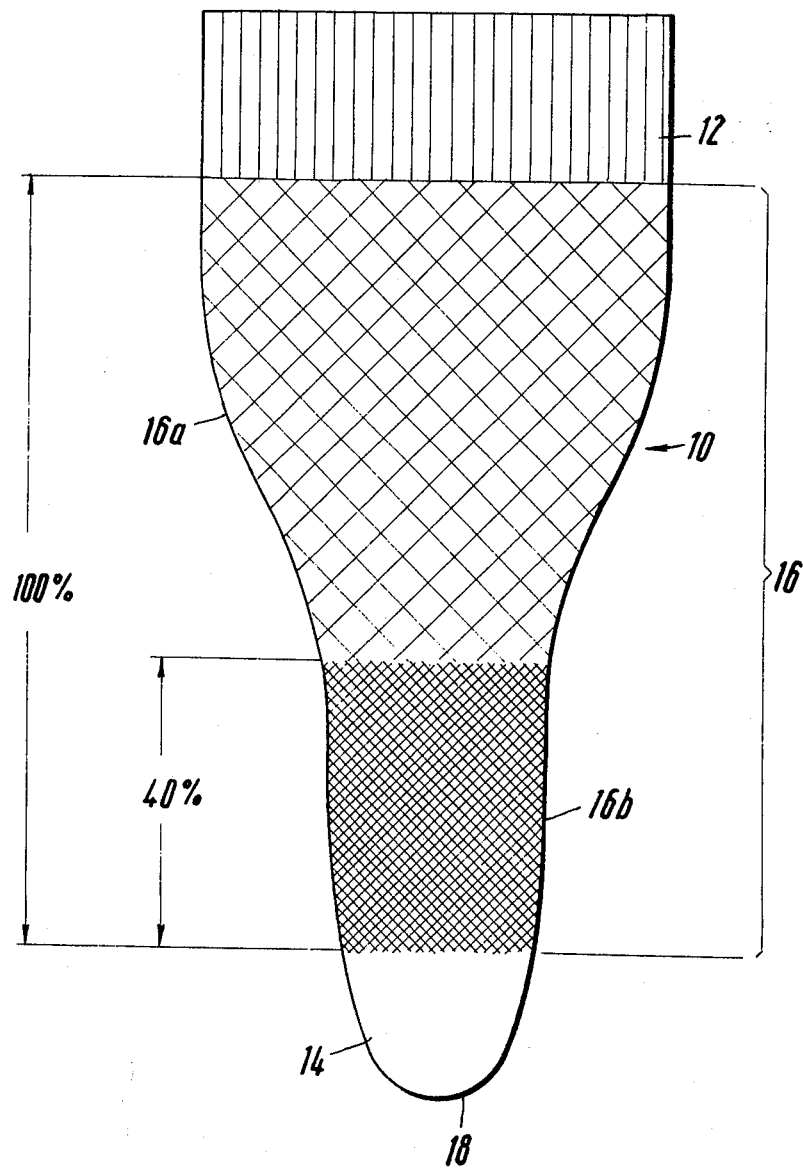

COMPRESSION SHEATH FOR BELOW KNEE AMPUTATED LIMBS

The present application is a continuation-in-part of my previous application Ser. No. 501,816 filed Aug. 29, 1974, abandoned which is, in turn, a continuation of my prior application 342,934 filed Mar. 2, 1973, now abandoned.

BACKGROUND OF THE INVENTION

The present invention relates generally to prosthetic aids and more particularly to a compression sheath particularly suitable for use upon below knee amputated limb stumps.

Nylon protective sheaths which are intended to prevent skin abrasion at points of contact with a prosthesis have been known for several years. When these prior art protective sheaths are applied, the sheaths are tightly pulled in an axial direction over an amputation stump so that the sheaths will envelop with a certain degree of tension the stump head at the end of the amputation stump.

The radial compressive forces which are required to be developed during use of the protective sheath upon a limb are necessarily a function of the axial forces which are developed by the sheath along the limb. However, in many cases an amputation stump may develop in the region of the stump head a strong hypersensitivity to the forces which are applied thereto. This is normally due to the condition of the ends of the nerve fibers which terminate immediately below the surface of the skin. Functional dependence of the radial compressive forces upon the axial forces thereby limits the radial compression which may appropriately be developed. That is, because of dependence of the radial forces upon the axial forces, and due to the hypersensitivity of the stump to the axial forces, the radial forces must, consequently, be limited so as not to develop discomforting axial pressure. As a result, the compression effect that may be exerted by the sheath will be limited and as a result there will not be insured a steadily increasing compression effect toward the stump end as would ordinarily be required to increase blood circulation.

It is therefore an object of the present invention to provide an improved structure for compressive sheaths adapted for use with below knee amputated limb stumps. The invention is intended to provide a compression sheath which will improve blood circulation of the injured limb during use of the sheath by developing an increasing compression force toward the end of the stump or limb. The sheath of the present invention is intended to simultaneously improve the sliding characteristics developed between the skin and the prosthetic aid in order to increase the comfort of the wearer during use of the prosthesis.

SUMMARY OF THE INVENTION

Briefly, the present invention may be described as a compression sheath for an amputee limb stump consisting essentially of a fabric formed from highly resilient yarn and having characteristics enabling the sheath to slide smoothly upon an amputee limb stump during use. More particularly, the sheath of the present invention comprises a first open end formed by a band defining an opening for insertion therethrough of a limb stump, a second closed end defined by an enclosed section of the sheath, and an intermediate section extending continuously between the band and the closed end. The intermediate section is, in accordance with a principal feature of the invention, comprised of a lower intermediate section extending contiguously from the enclosed section and an upper intermediate section extending between the band and the lower intermediate section. By a principal feature of the present invention the lower intermediate section is made with a knit pattern which has a higher yarn density than the upper intermediate section. The intermediate section is divided such that the lower section thereof extends over approximately 40% of its entire length while the upper intermediate section occupies about 60% of its length.

By a further aspect of the present invention, the yarn which is utilized to form the intermediate section is selected to have a yarn thickness within the range between about 30 to 44 dtex.

The material utilized in forming the intermediate section is preferably Nylon 66 HE crimped although, alternatively, Nylon 6 (Perlon) (crimped) may be used.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DESCRIPTION OF THE DRAWING

The single FIGURE of drawing is a longitudinal elevation showing the compression sheath according to the present invention and depicting the different yarn densities of the upper and lower portions of the intermediate section of the sheath.

DETAILED DESCRIPTION OF THE PREFERRED EMBODIMENTS

Referring now to the drawing there is shown a compression sheath generally labelled 10 comprising an upper open end defined by a band 12 and a lower closed end defined by an enclosed section 14 of the sheath. An intermediate section 16 extends continuously between the band 12 and the enclosed end 14. The intermediate section is composed of an upper intermediate section 16a and a lower intermediate 16b.

By an important feature of the present invention, the lower intermediate section 16b is formed with a knit pattern having a higher yarn density than the yarn density of the upper intermediate section 16a.

That is, the lower intermediate section 16b is formed with a greater number of stitches per square centimeter than the number of stitches per square centimeter provided in the upper intermediate section 16a.

As shown in the drawing, the lower intermediate section 16b extends across approximately 40% of the overall length of the intermediate section 16, which is indicated as 100% in the drawing. Of course, the upper intermediate section 16a will occupy approximately 60% of the overall length of the intermediate section 16.

As indicated in the drawing, the upper band 12 may be formed with a length of approximately 80 mm. The band is preferably made of non-run resistant material having a double hemmed construction.

Similarly, the lower enclosed end 14 of the sheath may be preferably formed with a length of approximately 80 mm and it also may be of non-run resistant material in order to enable proper formation therein of a closing seam 18.

When the sheath 10 is placed over an amputated limb, the upper band 12 will engage about the upper portion of the covered limb and apply a sufficient frictional force to maintain the sheath in place upon the limb. Because of the material utilized in forming the intermediate section 16, the balance of the sheath will create little or no frictional forces against the limb thereby preventing the creation of axial forces upon the limb. However, because of the resilient knit pattern of the yarn of the intermediate section 16, radial compression forces will be desirably developed about the circumference of the stump. Because of the fact that no axial forces against the limb are developed by the sheath, the lower enclosed end 14 will not be forced against the end of the limb or stump, thereby avoiding many of the problems arising with prior art devices.

As will be noted from the drawing, the sheath 10 is constructed with a diameter which progressively decreases from the upper band 12 toward the lower enclosed end 14.

The particular knit patterns which are produced in the intermediate section 16 enable proper compressive forces to be developed about the limb. Because of the narrower stitch pattern of the lower intermediate section 16b, a greater compressive force is developed by this section of the sheath about the limb of the wearer.

A further important feature of the present invention is the selection of the thickness of the yarn which is utilized to form the intermediate section 16 of the compression sheath. Yarn thickness has been found to be important for several reasons. First of all, proper selection of the yarn thickness will provide better protection against chafing of the skin of the stump upon which the sheath is utilized. By proper selection of the yarn thickness, medically desirable compression effects will be provided and, simultaneously, a sheath of greater durability will be produced.

In accordance with the present invention, it has been found that the most advantageous results are achieved by utilizing a yarn thickness within the range between about 30 to 44 dtex. It has been found that if the yarn thickness exceeds a maximum of 44 dtex, protection against chafing is reduced and the sliding effect of the sheath upon the limb is also reduced. A yarn thickness below the minimum level of 30 dtex will cause the durability of the sheath to deteriorate to an unacceptable extent. Selection of a yarn thickness below the minimum level will also cause deterioration of the compression effects which are desired.

In a preferred embodiment of the present invention, the yarn is selected to have a capillar yarn number of 13 with 398-needle construction. The preferred material utilized in making the sheath of the present invention is Nylon 66 HE crimped having a yarn thickness of 44 dtex. Alternatively, Nylon 6 (Perlon) (crinkled) may be used but, this alternative material will be found to have a lower crystalline melting point so that the natural stability of the material will be impaired if it is washed at too high a temperature.

The entire intermediate section 16 of the sheath should preferably be made to be run-resistant.

With a sheath constructed in accordance with the principles of the present invention, compression effects which are medically desirable will be achieved. The denser stitch pattern of the lower intermediate section 16b will produce a greater compressive effect at a portion of the limb stump at which such greater compression is desirable. Additionally, the upper intermediate section 16a will, in cooperation with the lower section, produce a lesser compressive effect with the overall pattern of the compression achieved being beneficial to the user. At the same time, the compressive effects are restricted to a radial direction about the limb stump and axial forces are virtually eliminated thereby preventing the lower enclosed section 14 from being pressed against the stump end with too great a force. Thus, any hypersensitivity of the stump end will not cause problems in the use of the sheath.

The material which is used for the sheath is a fabric having highly resilient yarns or threads with a low coefficient of friction thereby providing a superior sliding ability along the stump. Thus, the sheath reduces friction between the skin and the prosthetic aid and prevents abrasions which could be caused by such friction effects. Thus, again, radial compressive forces may be beneficially developed without causing detrimental axial forces in the longitudinal direction of the sheath.

In practice it has been found that maintenance of a maximum compression of 15 mm Hg. is desirable.

While specific embodiments of the invention have been shown and described in detail to illustrate the application of the inventive principles, it will be understood that the invention may be embodied otherwise without departing from such principles.

What is claimed is:

1. A compression sheath for an amputee limb stump consisting essentially of fabric of highly resilient yarn having characteristics enabling said sheath to slide smoothly upon an amputee limb stump upon which said sheath is applied, said sheath comprising a first open end formed by a band defining an opening for insertion therethrough of a limb stump, a second closed end defined by an enclosed section of said sheath, and an intermediate section extending continuously between said band and said enclosed end, said intermediate section being comprised of a lower intermediate portion extending contiguously from said enclosed section and an upper intermediate portion extending between said band and said lower intermediate portion, said lower intermediate portion being formed with a knitted pattern having a higher yarn density than said upper intermediate portion, said sheath having a diameter that progressively decreases from said open end towards said closed end, whereby said sheath when worn on a limb stump will produce an increasing radial compression force in a direction toward the end of the stump and said closed end without undesired axial frictional forces thereon.

2. A sheath according to claim 1 wherein said lower intermediate portion extends over about 40% of the length of said intermediate section.

3. A sheath according to claim 1 wherein said intermediate section is formed from yarn having a thickness greater than about 30 dtex.

4. A sheath according to claim 3 wherein the thickness of the yarn from which said intermediate section is formed is within a range between about 30 to 44 dtex.

5. A sheath according to claim 1 wherein said intermediate section is formed from Nylon 66 HE crimped.

6. A sheath according to claim 1 wherein said intermediate section is formed from Nylon 6 (Perlon) (crimped).

7. A sheath according to claim 1 wherein said intermediate section is constructed to produce a radial compressive force upon said amputee limb stump which is a maximum of 15mm Hg.

* * * * *